United States Patent [19]

Snaith et al.

[11] Patent Number: 5,206,394

[45] Date of Patent: Apr. 27, 1993

[54] LEWIS BASE COMPLEXES OF ALKALI METAL SALTS

[75] Inventors: Ronald Snaith; Dominic S. Wright, both of Cambridge, England

[73] Assignee: The Associated Octel Company Limited, London, United Kingdom

[21] Appl. No.: 372,362

[22] PCT Filed: Oct. 21, 1988

[86] PCT No.: PCT/GB88/00915

§ 371 Date: Aug. 18, 1989

§ 102(e) Date: Aug. 18, 1989

[87] PCT Pub. No.: WO89/03835

PCT Pub. Date: May 5, 1989

[30] Foreign Application Priority Data

Oct. 21, 1987 [GB] United Kingdom ............... 8724662

[51] Int. Cl.$^5$ ............................................. C07C 211/00
[52] U.S. Cl. ................................... 549/429; 549/505; 564/512; 564/14; 568/557; 568/606
[58] Field of Search ............... 549/429, 505; 564/512, 564/14; 566/557, 606, 668

[56] References Cited

U.S. PATENT DOCUMENTS

| | | | |
|---|---|---|---|
| Re. 28,456 | 7/1975 | Langer, Jr. et al. ............... | 260/563 |
| 3,734,963 | 5/1973 | Langer, Jr. et al. ............... | 260/573 R |
| 3,933,879 | 1/1976 | Langer, Jr. et al. ............... | 260/448 |
| 4,088,666 | 5/1978 | Langer, Jr. et al. ............... | 260/439 |
| 4,094,876 | 6/1978 | Langer, Jr. et al. ............... | 260/270 |
| 4,152,401 | 5/1979 | Langer, Jr. et al. ............... | 423/286 |
| 4,156,603 | 5/1979 | Langer, Jr. et al. ............... | 75/0.5 |
| 4,229,354 | 10/1980 | Bogdanovic ........................ | 549/501 |
| 4,301,081 | 11/1981 | Bogdanovic ........................ | 549/501 |
| 4,370,488 | 1/1983 | Bogdanovic ........................ | 549/501 |
| 5,045,244 | 9/1991 | Merlett ............................... | 260/665 G |

FOREIGN PATENT DOCUMENTS 2039005  1/1971  France.
WO7900696  9/1979  PCT Int'l Appl.

OTHER PUBLICATIONS

Magnus et al., "Alpha Lithiohexamethylphosphoric Triamide, etc.", Synthesis, No. 7, pp. 575–577, (Jul. 1980).
Barr et al., "The Isolation of a Highly Arene-Soluble Alkali Metal, etc.", J. Chem. Soc., Chem. Commun., pp. 127–129 (1986).
Barr, et al., "Crystal Structures of ($Ph_2C=NLi\cdot NC_5H_5)_4$, etc.", J. Chem. Soc., Chem. Commun., pp. 79–80 (1984).
Barr et al., "Synthesis, and Crystal and Solution Structures of the 1:1 TMEDA, etc.", J. Chem. Soc., Chem. Commun., pp. 145–147 (1988).
Snaith et al., "Reactions of Ammonium Salts with Butyllithium, etc.", J. Am. Chem. Soc., vol. 109, No. 25, pp. 7891–7893 (1987).

Primary Examiner—C. Warren Ivy
Assistant Examiner—Raymond Covington
Attorney, Agent, or Firm—Renner, Otto, Boisselle & Sklar

[57] ABSTRACT

Disclosed is a process for the manufacture of alkali metal salt complexes of the formula $(M_xX.nL)_y$, where M is an alkali metal, e.g. lithium, X is an anion, e.g. halide or thiocyanate, L is an organic electron-donating ligand (Lewis base), x is the valency of the anion X, n is usually 1,2 or 4 and y is an integer, by the in situ reaction of an alkali metal or an alkali metal hydride or alkyl, for example lithium, lithium hydride or butyl lithium, and an anhydrous ammonium salt comprising the anion X, e.g. an anhydrous ammonium halide, the reaction being performed in solution in an anhydrous solvent in the presence of the ligand (L).

12 Claims, No Drawings

LEWIS BASE COMPLEXES OF ALKALI METAL SALTS

This invention relates to the preparation of alkali metal salt complexes of the formula $(M_xX.nL)_y$, where M is an alkali metal, e.g. Li, Na or K, X is an anion, e.g. $F^-$, $Cl^-$, $Br^-$, $I^-$, $SCN^-$, $OCN^-$, $ClO_4^-$, $CO_3^{2-}$, L is a Lewis base, such as hexamethylphosphoramide (HMPA), tetramethylethylenediamine (TMEDA) or pentamethyldiethylenetriamine (PMDETA), x is the valency of the anion X, and is usually 1 or 2, n is usually 1, 2 or 4 and y is an integer up to infinity, depending upon the degree of lattice formation by the complex.

Alkali metal halide complexes of the above type are known: W. Setzer and P. v. R. Schleyer, Adv. Organomet. Chem. 1985, 24, 353; and are potentially useful commercial materials for a variety of purposes, particularly in the field of organic synthesis, where their solubility in organic media renders them useful as soluble, stoichiometrically controllable halogenating agents. This solubility is in marked contrast to the corresponding uncomplexed salts, e.g. the uncomplexed alkali metal halides, which are known to be high-melting-point materials often of extremely high lattice energy and therefore insoluble except in polar solvents. The Lewis base complexes of alkali metal salts are also of interest because of their low melting points in comparison with their uncomplexed precursors, and are potentially useful as low energy electrolytic sources of alkali metals: "Lithium: Current Applications in Science, Medicine and Technology", ed. R. O. Bach, Wiley, Chichester, 1985; they are potentially of great value as fast-ion conductors, e.g. in electrolyte and solvent systems for batteries, see Angew. Chem. Int. Ed. Engl. 25, 1986, No. 12, 1087-1089.

However, existing routes to such complexes are disadvantageous. For example, dissolution of uncomplexed alkali metal halides in neat donor or donor/hydrocarbon mixes requires total exclusion of water both from the halide and from the reaction system at large, both of which, in practice are extremely difficult to attain. In any case their frequently extremely high lattice energy often makes such dissolution impossible, D. Barr, W. Clegg, R. E. Mulvey and R. Snaith, J. Chem. Soc., Chem. Commun. 1984, 79; D. Barr, K. B. Hutton, J. H. Morris, R. E. Mulvey, D. Reed and R. Snaith, J. Chem. Soc., Chem. Commun. 1986, 127.

An alternative route involves the in situ formation of $(M.Hal)_y$ at low temperatures in the presence of the donor, the presence of which restricts the growth of the lattice, i.e. the value of y. According to this procedure an alkali metal organic compound, such as a lithium alkyl or an iminolithium complex, is reacted with a halide source, such as aluminium chloride or n-butyl bromide, in the presence of the ligand, e.g.:

$\underline{t}$-Bu$_2$C=NLi + AlCl$_3$ $\xrightarrow{\text{HMPA}}$ (LiCl.HMPA)$_4$ + Al product $\underline{n}$-BuLi + $\underline{n}$BuBr $\xrightarrow{\text{PMDETA}}$ (LiBr.PMDETA)$_2$ + Bu—Bu or C$_8$H$_{18}$ However, these routes are still highly susceptible to hydration problems and require extreme precautions to avoid the presence of water, which precautions are largely impracticable for commercial-scale operation. Not only that, but such processes represent an extremely inefficient utilisation of lithium, since the starting materials t-BuLi (which is used initially to prepare the t-Bu$_2$C=NLi by reaction with t-BuCN) and n-BuLi are themselves obtained by the reaction of a butyl halide with lithium, which produces lithium halide as a by-product, e.g.

(n or t)-BuHal + 2Li → (n or t)-BuLi + LiHal.

The present invention is based on the discovery of an alternative route for the preparation of Lewis base complexes of alkali metal salts, particularly lithium halide and thiocyanate complexes, that produces the complexes in high yield and high purity, and that does not apprently suffer from the hydration problems or product recovery problems associated with the known processes. In accordance with the present invention, alkali metal salt complexes of the formula $(M_xX.nL)_y$, where M is an alkali metal, X is an anion, L is an organic electron-donating ligand (Lewis base), x is the valency of the anion X, n is a number such that n:1 is the molar ratio of ligand to alkali metal salt in the complex, and y is an integer up to infinity are prepared by reacting an alkali metal or a hydride or alkyl thereof with an anhydrous ammonium salt of the anion X in the presence of the ligand (L), the reaction being carried out under anhydrous conditions and under an inert atmosphere and in the presence of a hydrocarbon solvent. n is usually 1, 2 or 4. The reaction scheme of the process of the invention may be illustrated as follows:

LiH + anhyd.NH$_4$Hal + nL $\longrightarrow$

H$_2$ + NH$_3$ + 1/y (LiHal.nL)$_y$

BuLi + anhyd.NH$_4$Hal + nL $\longrightarrow$

BuH + NH$_3$ + 1/y (LiHal.nL)$_y$

Na + anhyd.NH$_4$Hal + nL $\longrightarrow$

½H$_2$ + NH$_3$ + 1/y (NaHal.nL)$_y$

More than one alkali metal, more than one ammonium salt and/or more than one Lewis base may be used in the reaction, but the results may be less predictable in such cases.

The reaction, which occurs readily at moderately elevated temperatures, e.g. 40° C. to 60° C., is accompanied by vigorous evolution of gas, which is a mixture of butane and ammonia in the case of the alkali metal alkyl, e.g. butyllithium reactant and of hydrogen and ammonia in the case of the pure metal or the hydride, e.g. lithium hydride, reactant. This gas evolution probably helps to drive the reaction substantially to completion.

Following completion of the reaction, which is indicated by the cessation of gas evolution, the desired complex can be recovered from solution by crystallisation, preferably under conditions of refrigeration.

As to the requirement for anhydrous reagents and conditions, it is to be understood that normal commercial-grade anhydrous ammonium salts may be used. This is in contrast to the previous reaction procedures, where even analar-grade anhydrous lithium salts have to be subjected to further extensive drying in vacuo to eliminate even the last traces of moisture, before satisfactory yields of a non-hydrated product can be obtained.

In general, substantially stoichiometric quantities of the reagents will be used, and it is an additional feature of this invention that, in contrast to previous procedures, the stoichiometry of the final product can be controlled by the stoichiometry of the reaction mixture, in particular, the stoichiometric quantity of the ligand L, e.g. 1, 2 or 4 moles depending on the desired value for n.

As indicated, the process of the present invention is particularly applicable to the preparation of lithium complexes, i.e. complexes of the formula defined where M is Li. However, the process may also be applied to complexes of other alkali metals, e.g. Na or K, and such complexes are novel.

Similarly, the present invention is particularly directed to the preparation of the halide complexes, i.e. where X is $F^-$, $Cl^-$, $Br^-$ or $I^-$, but other anions may be used, e.g. monovalent anions such as $SCN^-$, $OCN^-$, $ClO_4^-$ and $BF_4^-$, and polyvalent anions such as $CO_3^{2-}$.

As the organic ligand L, there may be used any suitable organic electron donor (Lewis base) such as hexamethylphosphoramide (HMPA), tetramethylethylenediamine (TMEDA), pentamethyldiethylenetriamine (PMDETA), 1,2-dimethoxyethane (glyme), bis(2-methoxyethyl)ether (diglyme), dioxan, and tetrahydrofuran (THF). Other suitable electron donors (Lewis bases) will be apparent.

The reaction is carried out in an anhydrous hydrocarbon solvent, e.g. hexane, toluene or mixtures thereof, and under an inert atmosphere, e.g. under nitrogen.

The process of the present invention is illustrated by the following Examples. Crystal structures of all the products have been determined.

EXAMPLE 1

5.9 cm³ of a 1.7 mol/liter solution of n-butyl lithium in n-hexane (10 mmol n-BuLi) was charged under nitrogen to a reaction vessel, following which the n-hexane was removed by evaporation and replaced by toluene. HMPA was added in 1, 2, 3 or 4 molar equivalents relative to BuLi followed by 10 mmol solid anhydrous ammonium halide as indicated below. The reaction mixture was heated to 40° C. to 60° C., whereupon vigorous evolution of the n-butane and ammonia occurred, accompanied by numerous colour changes of the solution and gradual disappearance of the solid. At the termination of the reaction (cessation of gas evolution and complete dissolution of the solid) the resulting solution was refrigerated (−5° C.) to crystallise the lithium halide complex indicated. The results are tabulated below in Table 1. Spectral analysis of the solution at the end of the reaction and before crystallisation shows a complete absence of ammonium ions, thus indicating substantially 100% reaction.

TABLE 1

| mols. HMPA added | ammonium salt | complex formula | m.p. °C. | yield* % |
|---|---|---|---|---|
| 1 | NH₄Cl | | | |
| 2 | NH₄Cl | | | |
| 3 | NH₄Cl | (LiCl.HMPA)₄ | 142–144 | 83 |
| 4 | NH₄Cl | | | |
| 2 | NH₄Br | (LiBr.1.5HMPA)₂ | 70–72 | 60 |

TABLE 1-continued

| mols. HMPA added | ammonium salt | complex formula | m.p. °C. | yield* % |
|---|---|---|---|---|
| 4 | NH₄Br | (LiBr.4HMPA)_y | 50–52 | 56 |
| 2 | NH₄I | (LiI.2HMPA)_y | 63–65 | 64 |
| 4 | NH₄I | (LiI.4HMPA)_y | 141–143 | 94 |

*First batch yield, i.e. after cooling to −5° C. Continued cooling at −5° C. increases the yield still further. Addition of an alkane such as n-hexane at the end of the reaction period also aids crystallisation and leads to higher yields.

EXAMPLE 2

Anhydrous NH₄Cl was added to a suspension of uncomplexed lithium hydride in a mixture of HMPA (2 equivalents) and toluene and the mixture heated for 4 days at 110° C. After filtration and cooling (LiCl.HMPA)₄ was recovered at 51% yield, m.p. 142°–144° C.

By proceeding in accordance with Example 2, but using NH₄BF₄ instead of NH₄Cl, the complex (LiBF₄.4HMPA)_y, m.p. 120°–122° C., is obtained in yield about 65%.

By proceeding in accordance with Example 2, but using NH₄BF₄ instead of NH₄Cl and PMDETA instead of HMPA, the complex (LiBF₄.PMDETA)_y, m.p. 109°–110° C., can be obtained in yield about 30%.

EXAMPLE 3

Under anhydrous conditions and under nitrogen, a solution of 10 mmol of n-butyllithium in hexane was added to a frozen mixture of 0.76 g (10 mmol) solid ammonium thiocyanate, 10 ml of toluene and 3.58 g (20 mmol) of HMPA at −196° C. to produce an orange-red mixture. This slowly turned violet at about 0° C., then yellow, and then became colourless but slightly cloudy at 25° C., with vigorous evolution of gas. 10 ml of toluene was added and the mixture warmed to give a pale-yellow solution, which on cooling deposited cubic crystals of basic formula (LiNCS.2HMPA)₂, but solvated with toluene probably to (LiNCS.2HMPA. ½ toluene)₂, m.p. 68°–71° C. The yield averaged over several preparations was around 90%.

Following similar procedures, the following complexes were also obtained;

| | m.p. °C. | yield % |
|---|---|---|
| (LiSCN.TMEDA)_infinity | 168–171 | 87 |
| (LiSCN.PMDETA)_y | 154–156 | 95 |

Where, in the above product formulae, the value of y is not given, the degree of lattice formation in the product has not been determined.

EXAMPLE 4

Under anhydrous conditions and under nitrogen, a red solution of 5 mmol of n-butyllithium in 5 ml of toluene and 1.79 g (10 mmol) of HMPA was frozen. 0.49 g (5 mmol) of solid ammonium bromide was added. The mixture was then warmed to 50° C., with vigorous evolution of gas and colour change to violet, then sepia, and finally after about 15 minutes, clear and colourless. 5 ml of hexane and 7 ml of toluene was added, whereupon a yellow oil separated. On cooling, colourless crystals were formed. These were filtered off and found by chemical analysis and ¹H n.m.r. spectra to be of formula (LiBr.1.5HMPA 0.5 toluene)₂, m.p. 56°–58° C.

The yield was 60%. After washing the crystals with hexane and submitting them to an absolute pressure of 40 Pa (0.3 mm of mercury) for 30 minutes, some toluene solvate was removed to give material of formula (LiBr.1.5HMPA 0.35 toluene)$_2$, m.p. 70°-72° C.

EXAMPLE 5

By proceeding in a similar manner to that of Example 1, but using sodium hydride, ammonium tetrafluoroborate and HMPA, a complex of sodium tetrafluoroborate and HMPA is obtained.

EXAMPLE 6

By proceeding in a similar manner to that of Example 1, but using n-butyllithium and sodium hydride, ammonium thiocyanate and HMPA in the molar ratios 1:1:2:4, a crystalline complex containing both lithium and sodium is obtained. This, by analogy with the product of Example 3, is assumed to be [LiNa(SCN)$_2$.4HMPA]$_y$. It melts at 103°-104° C.

EXAMPLE 7

Metallic potassium, ammonium thiocyanate and HMPA in the molar ratio 1:1:5 are reacted together in toluene under nitrogen and under anhydrous conditions at 110° C. for 15 minutes to give a white crystalline material, m.p. 60° C., which has been identified as (KSCN)$_3$.5HMPA.

This experiment is repeated at 25° C. for 15 minutes, using potassium hydride instead of the metal. The same product is obtained. Yields are about 60% to 90% over two batches.

EXAMPLE 8

In a similar manner to that of Example 7, metallic lithium, ammonium thiocyanate and HMPA in the molar ratios 1:1:2 are reacted together in toluene at ambient temperature to give (LiSCN.2HMPA)$_2$ in 85% yield.

When lithium hydride is substituted for metallic lithium, reaction is slower but (LiSNC.2HMPA)$_2$ is obtained, although the yield is lower, viz 72%.

EXAMPLE 9

Metallic potassium, ammonium iodide and HMPA in the molar ratios 1:1:2 are reacted together in toluene under nitrogen under anhydrous conditions. Warming to 100° C. initiates a vigorous reaction and a white solid, assumed to be (KI.2HMPA)$_y$, is formed.

When n-butyllithium is used in an excess of THF as Lewis base, it must first be freed from hexane to avoid product precipitation.

Dioxan, THF and diglyme all give vigorous reactions with n-butyllithium and ammonium thiocyanate, a colourless crystalline complex of the form [LiSCN.n-(donor)]$_y$ being produced in each case.

As well as the complexes mentioned in the Examples, the following crystalline complexes have also been made and identified, only the value y remaining to be found.

(LiBr.TMEDA)$_y$ (LiI.TMEDA)$_y$ (NaSCN.PMDETA)$_y$

We claim:

1. A method for the preparation of alkali metal salt complexes of the formula (M$_x$X.nL)$_y$, where M is an alkali metal, X is an anion, L is an organic electron-donating ligand (Lewis base), x is the valency of the anion X, n is a number such that n:1 is the molar ratio of ligand to alkali metal salt in the complex, and y is an integer up to infinity, comprising the step of reacting an alkali metal or a hydride or alkyl thereof with an anhydrous ammonium salt of the anion X in the presence of the ligand (L), the reaction being carried out under anhydrous conditions and under an inert atmosphere and in the presence of a hydrocarbon solvent.

2. A method according to claim 1, wherein the product alkali metal complex is recovered in crystalline form by cooling the reaction medium at the termination of the reaction, and/or by the addition of alkane.

3. A method according to claim 1 wherein, in the formula, M is Li and X is halide or thiocyanate, and which comprises reacting lithium hydride or a lithium alkyl with an anhydrous ammonium halide or thiocyanate, the reaction being carried out under anhydrous conditions in a hydrocarbon solvent and in the presence of the ligand L.

4. A method according to claim 3, wherein the lithium reactant is n-butyllithium.

5. A method according to claim 1 wherein, in the formula, M is Na or K.

6. A method according to claim 1 wherein a mixture of sodium hydride and n-butyllithium is used as the alkali metal reactant and the ammonium salt is the thiocyanate.

7. A method according to claim 3, wherein, in which the ammonium salt is ammonium chloride, bromide, iodide, thiocyanate or fluoroborate.

8. A method according to claim 1, wherein which the ligand L is hexamethylphosphoramide (HMPA), tetramethylethylenediamine (TMEDA), pentamethyldiethylenetriamine (PMDETA), 1,2-dimethoxyethane (glyme), bis(2-methoxyethyl)ether (diglyme), dioxan, or tetrahydrofuran (THF).

9. A method according to claim 1, wherein the reaction solvent is n-hexane or toluene.

10. A method according to claim 5, in which the ammonium salt is ammonium chloride, bromide, iodide, thiocyanate or fluoroborate.

11. An alkali metal salt complex of the formula (M′$_x$X.nL)$_y$, wherein M′ is one or more alkali metals, at least one of which is other than lithium, X is an anion, L is an organic electron-donating ligand (Lewis base), x is the valency of the anion X, n is a number such that n:1 is the molar ratio of ligand to alkali metal salt in the complex, and y is an integer up to infinity.

12. A method for the preparation of alkali metal salt complexes of the formula (M$_x$X.nL)$_y$, where M is an alkali metal, X is F$^-$, Cl$^-$, Br$^-$, I$^-$, SCN$^-$, OCN$^-$, ClO$_4^-$, BF$_4^-$ or CO$_3^{-2}$, L is an organic electron-donating ligand (Lewis base), x is the valency of X, n is a number such that n:1 is the molar ratio of ligand to alkali metal salt in the complex, and y is an integer up to infinity, comprising the step of reacting an alkali metal or a hydride or alkyl thereof with an anhydrous ammonium salt of X in the presence of the ligand (L), the reaction being carried out under anhydrous conditions and under an inert atmosphere and in the presence of a hydrocarbon solvent.

* * * * *